United States Patent
Matuszok et al.

(10) Patent No.: US 11,172,905 B2
(45) Date of Patent: Nov. 16, 2021

(54) DOSE MODULATION

(71) Applicant: Siemens Healthcare GmbH, Erlangen (DE)

(72) Inventors: Dieter Matuszok, Weisendorf (DE); Anja Fritzler, Erlangen (DE); Martin Petersilka, Adelsdorf (DE)

(73) Assignee: Siemens Healthcare GmbH, Erlangen (DE)

(*) Notice: Subject to any disclaimer, the term of this patent is extended or adjusted under 35 U.S.C. 154(b) by 0 days.

(21) Appl. No.: 16/872,885

(22) Filed: May 12, 2020

(65) Prior Publication Data

US 2020/0367850 A1 Nov. 26, 2020

(30) Foreign Application Priority Data

May 20, 2019 (EP) ..................... 19175359

(51) Int. Cl.
| | | |
|---|---|---|
| *A61B 6/00* | (2006.01) | |
| *H01J 35/30* | (2006.01) | |
| *H05G 1/30* | (2006.01) | |
| *H01J 35/14* | (2006.01) | |
| *A61B 6/03* | (2006.01) | |

(52) U.S. Cl.
CPC ............ *A61B 6/542* (2013.01); *A61B 6/4021* (2013.01); *H01J 35/30* (2013.01); *H05G 1/30* (2013.01); *A61B 6/032* (2013.01); *A61B 6/40* (2013.01); *A61B 6/4007* (2013.01); *H01J 35/153* (2019.05); *H01J 2235/086* (2013.01)

(58) Field of Classification Search
CPC ........ A61B 6/542; A61B 6/4021; H05G 1/30; H01J 35/30
See application file for complete search history.

(56) References Cited

U.S. PATENT DOCUMENTS

| | | | |
|---|---|---|---|
| 6,222,907 B1* | 4/2001 | Gordon, III | A61B 6/4225 378/116 |
| 2004/0208288 A1* | 10/2004 | Lenz | H01J 9/02 378/121 |
| 2009/0220051 A1 | 9/2009 | Kutschera | |
| 2010/0067651 A1* | 3/2010 | Hsieh | A61B 6/4085 378/17 |
| 2011/0122992 A1 | 5/2011 | Hanke et al. | |
| 2020/0098538 A1 | 3/2020 | Fritzler et al. | |

FOREIGN PATENT DOCUMENTS

| | | |
|---|---|---|
| DE | 102008011841 A1 | 10/2009 |
| DE | 102008033150 A1 | 2/2010 |
| DE | 102012211285 B3 | 10/2013 |
| DE | 102014219196 A1 | 1/2016 |
| EP | 3629361 A1 | 4/2020 |

* cited by examiner

*Primary Examiner* — Chih-Cheng Kao
(74) *Attorney, Agent, or Firm* — Harness, Dickey & Pierce, P.L.C.

(57) ABSTRACT

A method, in an embodiment, is for setting an X-ray intensity using a structured anode or a field emitter cathode or a finger-shaped cathode head. Other embodiments include an associated X-ray device, an associated single X-ray tube CT scanner, an associated dual X-ray tube CT scanner, and an associated computer program product.

16 Claims, 3 Drawing Sheets

DOSE MODULATION

PRIORITY STATEMENT

The present application hereby claims priority under 35 U.S.C. § 119 to European patent application number EP 19175359.9 filed May 20, 2019, the entire contents of which are hereby incorporated herein by reference.

FIELD

Embodiments of the invention generally relate to a method for setting an X-ray intensity using a structured anode or a field emitter cathode or a finger-shaped cathode head; an associated X-ray device; an associated single X-ray tube CT scanner; an associated dual X-ray tube CT scanner; and an associated computer program product.

BACKGROUND

An X-ray imaging scan of a patient may require modulation of the X-ray dose. Dose modulation usually involves adjusting the X-ray intensity, in particular according to the patient, during the imaging scan. The dose can usually be modulated by varying a heating current of an emitter and/or of an emitter heater. In a conventional X-ray tube, the speed of the dose modulation is limited in particular by thermal properties of the emitter and/or emitter heater of the X-ray tube. For example, by way of the heating current flowing in the emitter heater, a conventional flat emitter can be heated indirectly by heating electrons emerging from the conventional emitter heater, thereby exciting the emission of electrons from the conventional flat emitter. An alternative flat emitter or a conventional emitter typically carries the heating current directly, thereby causing it to emit electrons.

The more significantly the X-ray intensity is changed, the longer this process usually takes because of the comparatively sluggish thermal response. In particular, a significant reduction in the X-ray intensity can take some tenths of a second in the conventional X-ray tube. If, for example, the conventional X-ray tube is used in a CT scanner, for a rotation time of the conventional X-ray tube in the CT scanner in the sub-second range, the dose modulation cannot always be instantaneously matched to the patient in this case.

SUMMARY

Embodiments of the invention are directed to a method for setting an X-ray intensity using a structured anode or a field emitter cathode or a finger-shaped cathode head; an associated X-ray device; an associated single X-ray tube CT scanner; an associated dual X-ray tube CT scanner; and an associated computer program product, thereby enabling the X-ray intensity to be determined more quickly.

Advantageous embodiments are described in the claims.

The method according to at least one embodiment of the invention is for setting an X-ray intensity, comprising:

providing an X-ray tube which comprises a structured anode having a first anode microstructure and a second anode microstructure, providing a first X-ray intensity number according to the first anode microstructure and a second X-ray intensity number according to the second anode microstructure in a controller, determining a first X-ray intensity setpoint in the controller according to a patient undergoing an imaging scan, selecting the first X-ray intensity number or the second X-ray intensity number as a first setpoint X-ray intensity number according to the first X-ray intensity setpoint in the controller, and aligning an electron beam of the X-ray tube to the first anode microstructure or to the second anode microstructure according to the first setpoint X-ray intensity number selected for generating the X-rays, thereby setting the X-ray intensity of the structured anode.

The X-ray device according to an embodiment of the invention comprises in particular the X-ray tube and the controller. The controller is typically connected to the X-ray tube, in particular to the deflector, for aligning the electron beam. The X-ray device has an X-ray detector with the X-ray detector read time. The X-ray tube and the X-ray detector are advantageously matched to one another via the controller during the imaging scan. The X-ray tube can in particular incorporate the electromagnetic deflector or the Wehnelt cylinder as a deflector.

The method according to at least one embodiment of the invention for setting an X-ray intensity comprising a field emitter cathode comprises:

providing a field emitter cathode, providing an X-ray intensity characteristic as a function of an emitter voltage dropped across the field emitter cathode in a controller, determining an X-ray intensity setpoint in the controller according to a patient undergoing an imaging scan, selecting the emitter voltage from the X-ray intensity characteristic according to the X-ray intensity setpoint, and applying the emitter voltage selected to the field emitter cathode, thereby setting the X-ray intensity.

The method according to at least one embodiment of the invention for setting an X-ray intensity using a finger-shaped cathode head comprises:

providing a meander-shaped flat emitter having a finger-shaped cathode head, providing, in a controller, an X-ray intensity characteristic as function of a reverse voltage dropped across the finger-shaped cathode head, determining an X-ray intensity setpoint in the controller according to a patient undergoing an imaging scan, selecting the reverse voltage from the X-ray intensity characteristic according to the X-ray intensity setpoint, and applying the reverse voltage selected to the finger-shaped cathode head, thereby setting the X-ray intensity.

The computer program product according to at least one embodiment of the invention can be directly loaded into a memory of a at least one processor and has program code segments for carrying out a method for setting an X-ray intensity when the computer program product is executed in the at least one processor. The controller can incorporate the at least one processor.

The computer program product can be a computer program or comprise a computer program. The computer program product has in particular the program code segments which constitute the method steps according to the invention. As a result, the method according to at least one embodiment of the invention can be carried out in a defined and repeatable manner and control can be exercised over onward transmission of the method according to at least one embodiment of the invention.

The computer program product is preferably configured such that the at least one processor can carry out the method steps according to at least one embodiment of the invention via the computer program product. The program code segments can in particular be loaded into a memory of the at least one processor and typically executed via a processor of the at least one processor with access to the memory. When the computer program product, in particular the program code segments, is executed in the at least one processor, typically all the inventive embodiments of the method can be implemented.

Features, advantages or alternative embodiments mentioned in the description of the apparatus are likewise applicable to the method and vice versa. In other words, claims relating to the method cam be further developed using features of the apparatus and vice versa. In particular, embodiments of the inventive apparatus can be used in embodiments of the method.

BRIEF DESCRIPTION OF THE DRAWINGS

The invention will now be described and explained in greater detail with reference to the example embodiments illustrated in the figures. In the following description of the figures, structures and entities that remain essentially identical are denoted by the same reference character as at the first occurrence of the respective structure or entity.

DETAILED DESCRIPTION OF THE EXAMPLE EMBODIMENTS

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuity such as, but not limited to, a processor, Central At least one processor (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/ hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central At least one processor (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer at least one processors into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

The method according to at least one embodiment of the invention is for setting an X-ray intensity using a structured anode, comprising:

providing an X-ray tube which comprises a structured anode having a first anode microstructure and a second anode microstructure, providing a first X-ray intensity number according to the first anode microstructure and a second X-ray intensity number according to the second anode microstructure in a controller, determining a first X-ray intensity setpoint in the controller according to a patient undergoing an imaging scan, selecting the first X-ray intensity number or the second X-ray intensity number as a first setpoint X-ray intensity number according to the first X-ray intensity setpoint in the controller, and aligning an electron beam of the X-ray tube to the first anode microstructure or to the second anode microstructure according to the first setpoint X-ray intensity number selected for generating the X-rays, thereby setting the X-ray intensity of the structured anode.

A particular advantage of an embodiment of the method for setting the X-ray intensity using the structured anode is that the X-ray intensity can be set quickly, particularly compared to varying the heating current. This is in particular because the electron beam can usually be aligned, i.e. moved, more quickly than a heating current of a conventional emitter and/or of a conventional emitter heater can be varied and/or than the electron emission rate can be adapted according to the varying of the heating current because of the thermal characteristics. Varying the heating current is usually slower than aligning the electron beam. The X-ray intensity can advantageously be set/varied even though the heating current is not changed, which means that the number of electrons emitted typically remains constant. In particular, the inventive method for setting the X-ray intensity therefore provides particularly advantageous dose modulation.

Dose modulation describes in particular adjusting the X-ray intensity subject to the condition that the dose for the patient during the imaging scan is preferably reduced continuously to a level ensuring the diagnostic usefulness of a medical image acquired according to the X-ray intensity. The imaging scan involves in particular irradiating the patient in order to be able to reconstruct the medical image of the patient. The imaging scan can be contrast-agent-aided and/or dynamic. The medical image can be in DICOM format after reconstruction. The dose is advantageously modulated during the imaging scan.

The structured anode can be a stationary anode or rotating anode. The rotating anode can comprise in particular a type of rotary piston X-ray tube and/or rotating anode X-ray tube. To generate the X-rays, the structured anode typically has tungsten or molybdenum, or other suitable materials, on at least one surface aligned toward the electron beam. The X-ray tube is usually vacuumized. The X-ray tube typically has a cathode with an emitter for providing the electron beam. The electron beam usually transports electrons from the emitter to the structured anode in the vacuum of the X-ray tube, in particular as a function of an acceleration voltage. The emitter can be in particular a field effect emitter, a flat emitter or a filament-type emitter. The flat emitter can in particular be implemented using a cathode according to DE 10 2008 011 841 A1, the entire contents of which are hereby incorporated herein by reference.

The first anode microstructure and/or the second anode microstructure can be created, for example, when the structured anode is manufactured or the structured anode can be appropriately processed subsequently. The first anode microstructure and/or the second anode microstructure describe in particular local changes, e.g. in the micrometer range, particularly on the surface of the structured anode. The first anode microstructure can comprise, for example, a plurality of local changes, while the second anode microstructure comprises no local change. The structured anode is disclosed, for example, in the unpublished application EP 18196848, the entire contents of which are hereby incorporated herein by reference.

Providing the X-ray tube can include manufacturing of the X-ray tube. Alternatively or in addition, providing the X-ray tube can include setting up the X-ray tube, in particular for an imaging scan. The setting-up can include placing a patient to be examined by the imaging scan in the vicinity of the X-ray tube. Providing the X-ray tube includes in particular using the X-ray tube during the imaging scan. The setting-up and/or use can be performed in particular by a user and/or a physician.

The first X-ray intensity number and the second X-ray intensity number describe, in particular, an efficiency with which electrons of the electron beam that are incident on the anode microstructure of the structured anode are converted into X-rays. The first X-ray intensity number and/or the second X-ray intensity number can in each case include an X-ray intensity characteristic. The first X-ray intensity number and second X-ray intensity number correlate in particular with an X-ray dose and/or are preferably different so as to enable the dose to be modulated. The first X-ray intensity number and the second X-ray intensity number preferably differ in such a way that the X-ray intensity is preferably dependent on the anode microstructure selected. The first X-ray intensity number and the second X-ray intensity number are advantageously independent of electron beam intensity. A separate X-ray intensity number is usually provided for each anode microstructure. For example, the X-ray intensity is stronger the higher the X-ray intensity number.

The X-ray intensity number can in particular be dependent on the acceleration voltage. In particular, the acceleration voltage can influence the first X-ray intensity number and the second X-ray intensity number in such a way that a ratio of the first X-ray intensity number to the second X-ray intensity number is likewise dependent on the acceleration voltage. For example, at an acceleration voltage of 120 kV the ratio can be 60/100 or, at 80 kV, 70/90 relative to a maximum value. The X-ray intensity number depends in particular on the anode microstructure's shape. The X-ray intensity number typically depends on a free path length and/or a scattering coefficient of the electron beam in the anode microstructure.

Providing the X-ray intensity number can include in particular retrieving the first X-ray intensity number and/or retrieving the second X-ray intensity number from a memory unit. It is basically conceivable for the first X-ray intensity number and the second X-ray intensity number to be determined by the manufacturer of the X-ray tube, in particular of the structured anode, and stored in the memory unit. The first X-ray intensity number and/or the second X-ray intensity number can be advantageously determined e.g. by the user and/or the physician during a reference scan. The reference scan can include another imaging scan of a phantom and/or of another patient. Providing the X-ray intensity number can include modeling and/or simulating the structured anode. The memory unit can be part of the X-ray tube. The providing includes in particular providing the first X-ray intensity number and the second X-ray intensity number as input parameters for selecting the first X-ray intensity number or the second X-ray intensity number.

The first X-ray intensity setpoint describes in particular a predefined target value of the X-ray intensity after alignment of the electron beam. The first setpoint specifies in particular the X-ray intensity. The first setpoint can depend in particular on the patient's anatomy and/or physiology. For example, the first setpoint can be dependent on an ECG signal of the patient's physiology. Alternatively or in addition, the first setpoint can depend on the patient's dimensions or an anatomical structure of the patient along the X-ray direction. The anatomical structure describes in particular an organ and/or a bone and/or a vessel. The first setpoint is higher the more radiopaque the anatomical structure or the patient depending on the orientation of the X-rays. For example, the patient is more radiopaque in the case of X-raying parallel to the patient's shoulder than in the case of frontal X-raying of the patient's abdomen.

The controller is designed in particular to determine the first setpoint, in particular according to a setpoint algorithm. For example, the controller can take into account a signal of a physiological measuring system when determining the first setpoint. The physiological measuring system can advantageously acquire the patient's physiology, in particular the ECG signal and/or respiration. Alternatively or in addition, the controller can determine the first setpoint of the intensity e.g. via a medical plain film X-ray. The medical plain film X-ray can be equivalent to a localizer image or an older medical image of the patient and/or preferably shows the patient's anatomy. It is basically conceivable for the first setpoint to depend e.g. on a rotation angle of the X-ray tube. The first setpoint can be determined subject to the proviso of reducing the dose for the patient.

Selecting the first X-ray intensity number or the second X-ray intensity number includes in particular comparing the first X-ray intensity setpoint with the first X-ray intensity number and the second X-ray intensity number, wherein, for example, two difference values are calculated and the lower value in absolute terms is selected. The first setpoint X-ray intensity number is preferably identifiable by the lower difference value in absolute terms. In other words, the X-ray intensity number which is preferably closest in absolute terms to the X-ray intensity setpoint, or particularly advantageously equates thereto, is preferably selected. If the difference values are identical, the X-ray intensity number of the not previously irradiated anode microstructure is selected, for example, in order to ensure a uniform heat distribution. The first setpoint X-ray intensity number typically corresponds to the first X-ray intensity number selected or to the second X-ray intensity number selected. The controller is typically designed to select the setpoint X-ray intensity number.

The controller is in particular connected to a deflector of X-ray tube for aligning the electron beam. Aligning the electron beam describes in particular determining a focal point of the electron beam on the structured anode. The focal point advantageously coincides with the first anode microstructure and/or the second anode microstructure. In particular, the focal point encompasses the first anode microstructure and/or the second anode microstructure. The electron beam can typically be optionally aligned to the first anode microstructure or to the second anode microstructure, causing the electrons to be preferably incident on the first anode microstructure or on the second anode microstructure. It is basically conceivable for a local distribution of the electron beam to be selected such that the electron beam at least partially or completely covers the first anode microstructure or the second anode microstructure, or at least partially or completely covers the first anode microstructure and the second anode microstructure together. The electron beam may strike an area on the structured anode outside the first anode microstructure and/or the second anode microstructure. Aligning the electron beam via the deflector is particularly fast compared to varying the heating current.

When the electrons of the electron beam impinge on the target, X-rays with an intensity according to the respective X-ray intensity number are typically generated. Aligning the electron beam in particular sets the X-ray intensity because the X-ray intensity typically correlates with the respective X-ray intensity number.

One embodiment provides that a second X-ray intensity setpoint is determined in the controller according to the patient being examined during the imaging scan, wherein a second setpoint X-ray intensity number is selected according to the second X-ray intensity setpoint in the controller and wherein the electron beam of the X-ray tube is re-aligned to the first anode microstructure or to the second anode microstructure according to the second setpoint X-ray intensity number selected. This embodiment is advantageous in that the X-ray intensity can be changed by the re-setting. Particularly if a plurality of medical images and/or a plurality of X-ray projections are to be acquired depending on the X-rays generated during the imaging scan, this embodiment is advantageous because the X-ray intensity can be adjusted for each medical image and/or each X-ray projection. The re-aligning of the electron beam according to the second setpoint X-ray intensity number selected typically takes place after the aligning of the electron beam according to the first setpoint X-ray intensity number selected. The second setpoint can be determined when the first setpoint is determined or thereafter. The second setpoint X-ray intensity number typically corresponds to the first X-ray intensity number selected or to the second X-ray intensity number selected. It is basically conceivable for the electron beam to be repeatedly aligned or to remain unchanged.

One embodiment provides that the electron beam is re-aligned according to the selected second setpoint X-ray intensity number within an electron beam aligning time of less than 1 s after alignment of the electron beam according to the first setpoint X-ray intensity number selected. This embodiment typically enables it to be re-aligned during the same imaging scan.

One embodiment provides that the electron beam aligning time is less than 1 ms. The electron beam aligning time can in particular be between 1 and 900 µs, preferably between 10 and 100 µs. This embodiment is particularly advantageous because the electron beam aligning time is of the same order of magnitude as the X-ray detector read time. The X-ray detector read time is, for example, less than 1 ms or more specifically between 100 and 300 µs.

One embodiment provides that the electron beam aligning time is matched to the X-ray detector read time of the imaging scan. In this embodiment the electron beam can be aligned, for example, in sync with read-out of the X-ray detector. This embodiment therefore provides advantages particularly when the plurality of medical images and/or the plurality of X-ray projections are acquired. In fact, the acquisition of a single X-ray projection typically takes as long as the X-ray detector read time. The medical image typically comprises a large number of X-ray projections. Accordingly, a single medical image typically takes a plurality of X-ray detector read times to acquire.

One embodiment provides that the first anode microstructure differs from the second anode microstructure in at least one of the following parameters:
groove depth,
groove width,
center point distance,
in a dotting of a groove. This embodiment describes in particular making easily implemented local changes on the surface of the structured anode, in particular of the first anode microstructure and of the second anode microstructure. The local changes on the surface can in particular describe the shape of the anode microstructure. The groove depth is, for example, in the range between 0.1 and 1000 µm, preferably between 1 and 100 µm, particularly advantageously between 10 and 15 µm. The groove width is, for example, in the range between 0.1 and 1000 µm, preferably between 1 and 100 µm, particularly advantageously between 10 and 15 µm.

The difference in the center point distance is advantageous particularly in combination with a different angle of incidence of the electron beam. The center point distance describes in particular a distance from a center point or a reference point of the structured anode. If the structured anode corresponds to the rotating anode, for example, the center point is a point on the axis of rotation of the rotating anode.

Alternatively, if the structured anode is the stationary anode, the reference point corresponds, for example, to a point on a straight line defined by the first anode microstructure and the second anode microstructure, wherein the point does not lie between the first anode microstructure and the second anode microstructure and, as a result, the angle of incidence of the electron beam typically varies. The efficiency of X-ray generation is typically lower the more pronounced the dotting. The dotting therefore provides in particular a simple way of adjusting the X-ray intensity. The dotting can encompass, for example, 1 to 50%, advantageously 10 to 20% of the groove width or of a groove length. For example, the first anode microstructure can be flat and the second anode microstructure can have one and/or a plurality of grooves. Each groove can have the same groove width or the same groove depth or alternatively different groove widths and/or different groove depths. The number of grooves of the first anode microstructure can be equal to the number of grooves of the second anode microstructure.

One embodiment provides that the electron beam is aligned via an electromagnetic deflector or via a Wehnelt cylinder. The electromagnetic deflector can in particular incorporate a magnetic quadrupole. In this case the X-ray tube advantageously contains the electromagnetic deflector or the Wehnelt cylinder. This embodiment is particularly advantageous because it allows rapid deflection of the electron beam according to the electron beam aligning time. The electromagnetic deflector or the Wehnelt cylinder are in particular connected to the controller.

One embodiment provides that another structured anode having a third anode microstructure and a fourth anode microstructure is provided as part of another X-ray tube, wherein a third X-ray intensity number according to the third anode microstructure and a fourth X-ray intensity number according to the fourth anode microstructure is provided in the controller, wherein another setpoint of an X-ray intensity of the other structured anode is determined in the controller in a complementary manner to the first setpoint, wherein the third X-ray intensity number or the fourth X-ray intensity number is selected in the controller as another setpoint X-ray intensity number according to the other X-ray intensity setpoint, and wherein another electron beam of the other X-ray tube is aligned to the third anode microstructure or to the fourth anode microstructure according to the other setpoint X-ray intensity number selected for generating the X-rays, thereby setting the X-ray intensity of the other structured anode.

This embodiment describes in particular the operation of the other X-ray tube alternately with the X-ray tube because of the complementary determining of the other setpoint. Essentially, therefore, the X-ray tube and the other X-ray tube are preferably of identical design and/or are in particular operated synchronously. The X-ray tube and the other X-ray tube are in particular implemented separately for setting the X-ray intensity, e.g. in the controller. This embodiment indicates in particular that the other X-ray intensity setpoint of the other structured anode is determined in the controller in a complementary manner to the first setpoint.

The complementary determining means in particular that the X-ray intensity of the X-ray tube is reduced if the X-ray intensity of the other X-ray tube this increased. This provides an advantageous way of positively influencing the scatter to primary radiation ratio of the X-ray tube and the other X-ray tube because the alternation reduces the amount of scattered radiation, in particular without changing the heating current. As a result, the power reserve of the X-ray tube in alternation is retained because the electron beam is aligned to a comparatively lower intensity anode microstructure in order to reduce the X-ray intensity without having to reduce the heating current.

The X-ray device according to an embodiment of the invention comprises in particular the X-ray tube and the controller. The controller is typically connected to the X-ray tube, in particular to the deflector, for aligning the electron beam. The X-ray device has an X-ray detector with the X-ray detector read time. The X-ray tube and the X-ray detector are advantageously matched to one another via the controller during the imaging scan. The X-ray tube can in particular incorporate the electromagnetic deflector or the Wehnelt cylinder as a deflector.

The single X-ray tube CT scanner of at least one embodiment comprises in particular the X-ray device. In this case the X-ray device typically rotates at least partially around the patient. In particular, in this case the first setpoint can depend on the angle of rotation of the X-ray tube.

In at least one embodiment, the X-ray device of the dual X-ray tube CT scanner typically comprises, in addition to the X-ray tube, the other X-ray tube. The X-ray tube and the other X-ray tube can basically be of identical design and yet be operated alternately. This is particularly advantageous if the intensity of the two X-ray tubes is adjusted alternately in order to optimize the scatter to primary radiation ratio.

The method according to at least one embodiment of the invention for setting an X-ray intensity comprising a field emitter cathode comprises:

providing a field emitter cathode, providing an X-ray intensity characteristic as a function of an emitter voltage dropped across the field emitter cathode in a controller, determining an X-ray intensity setpoint in the controller according to a patient undergoing an imaging scan, selecting the emitter voltage from the X-ray intensity characteristic according to the X-ray intensity setpoint, and applying the emitter voltage selected to the field emitter cathode, thereby setting the X-ray intensity.

The field emitter cathode typically has field emitter cathode nanotubes containing e.g. silicon or carbon. The electron beam of the field emitter cathode is typically generated such that a comparatively low emitter voltage (40 to 100 V) is applied to the field emitter cathode, thereby producing a strong electrical field within the field emitter cathode, in particular between the field emitter cathode nanotubes, with the electrons being emitted. This method is advantageous inasmuch as the comparatively low emitter voltage can be quickly applied or removed. In comparison to the method for setting the X-ray intensity using the structured anode, usually the intensity of the electron beam is adjusted instead of aligning the electron beam. This can be advantageous in particular because the controlling of the intensity of the electron beam is decoupled from the focusing of the electron beam.

The method according to at least one embodiment of the invention for setting an X-ray intensity using a finger-shaped cathode head comprises:

providing a meander-shaped flat emitter having a finger-shaped cathode head, providing, in a controller, an X-ray intensity characteristic as function of a reverse voltage dropped across the finger-shaped cathode head, determining an X-ray intensity setpoint in the controller according to a patient undergoing an imaging scan, selecting the reverse voltage from the X-ray intensity characteristic according to the X-ray intensity setpoint, and applying the reverse voltage selected to the finger-shaped cathode head, thereby setting the X-ray intensity.

Particularly if the meander-shaped flat emitter is designed according to DE 10 2008 011 841 A1, the emission of electrons can be rapidly suppressed by way of the reverse voltage of, for example, between 10 V and 5 kV, advantageously between 100 V and 2 kV, applied to the cathode head. Applying a reverse voltage to a conventional cathode head having a curved emitter is disclosed, for example, in DE 10 2012 211 285 B3, the entire contents of which are hereby incorporated herein by reference.

This embodiment is particularly advantageous in that the meander-shaped flat emitter with the finger-shaped cathode head can be deactivated at comparatively low reverse voltages. Because of the (in absolute terms) low reverse voltage, the electron beam, in particular the extent of the electron beam, is advantageously kept constant. For example, the embodiment allows parallel electron beam emission independently of the reverse voltage. It is basically conceivable for the previous extent of the electron beam to be reproduced via the deflector after the reverse voltage selected has been applied. This embodiment is advantageous particularly in respect of image quality. The selection of reverse voltage can include in particular partial and/or complete deactivation of the electron beam. Partial deactivation of the electron beam can equate in particular to dimming of the electron beam.

The computer program product according to at least one embodiment of the invention can be directly loaded into a memory of a at least one processor and has program code segments for carrying out a method for setting an X-ray intensity when the computer program product is executed in the at least one processor. The controller can incorporate the at least one processor.

The computer program product can be a computer program or comprise a computer program. The computer program product has in particular the program code segments which constitute the method steps according to the invention. As a result, the method according to at least one embodiment of the invention can be carried out in a defined and repeatable manner and control can be exercised over onward transmission of the method according to at least one embodiment of the invention.

The computer program product is preferably configured such that the at least one processor can carry out the method steps according to at least one embodiment of the invention via the computer program product. The program code segments can in particular be loaded into a memory of the at least one processor and typically executed via a processor of the at least one processor with access to the memory. When the computer program product, in particular the program code segments, is executed in the at least one processor, typically all the inventive embodiments of the method can be implemented.

The computer program product is stored, for example, on a physical, computer-readable medium and/or provided digitally as a data package in a computer network. The computer program product can be the physical, computer-readable medium and/or the data package in the computer network. Thus, the invention can also proceed from the physical, computer-readable medium and/or the data package in the computer network. The physical, computer-readable medium can usually be connected directly to the at least one processor, e.g. by inserting the physical, computer-readable medium into a DVD drive or USB port, thereby providing the at least one processor with, in particular, read access to the physical, computer-readable medium. The data package can preferably be invoked from the computer network. The computer network can contain the at least one processor or can be indirectly connected to the at least one processor via a wide area network (WAN) or a (wireless) local area network connection (WLAN or LAN). For example, the computer program product can be stored digitally on a cloud server at a storage location of the computer network, transferred via the WAN via the Internet and/or via the WLAN or LAN to the at least one processor in particular by following a download link to the storage location of the computer program product.

Features, advantages or alternative embodiments mentioned in the description of the apparatus are likewise applicable to the method and vice versa. In other words, claims relating to the method cam be further developed using features of the apparatus and vice versa. In particular, embodiments of the inventive apparatus can be used in embodiments of the method.

Figure 1:
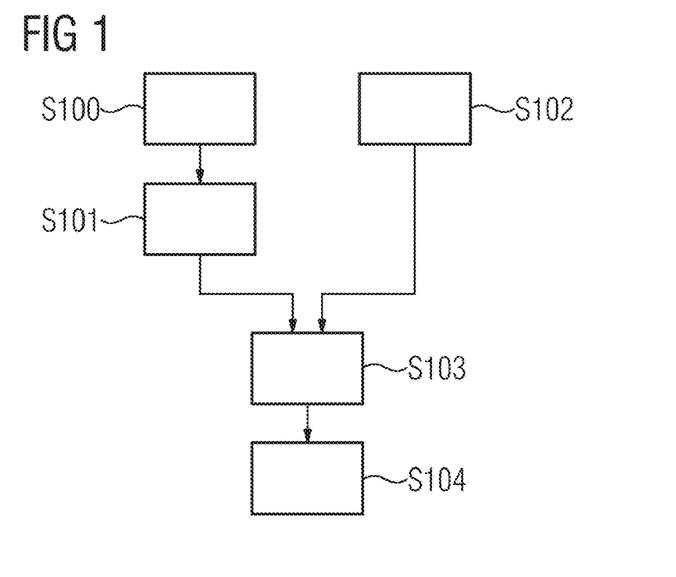
FIG. 1 shows a flowchart of a method for setting an X-ray intensity using a structured anode in a first example embodiment.

FIG. 1 shows a flowchart of a method for setting an X-ray intensity using a structured anode in a first example embodiment.

Method step S100 denotes providing an X-ray tube comprising a structured anode having a first anode microstructure and a second anode microstructure.

Method step S101 denotes providing a first X-ray intensity number according to the first anode microstructure and a second X-ray intensity number according to the second anode microstructure in a controller.

Method step S102 denotes determining a first X-ray intensity setpoint in the controller according to a patient undergoing an imaging scan.

Method step S103 denotes selecting the first X-ray intensity number or the second X-ray intensity number as a first setpoint X-ray intensity number according to the first X-ray intensity setpoint in the controller.

Method step S104 denotes aligning an electron beam of the X-ray tube to the first anode microstructure or to the second anode microstructure according to the first setpoint X-ray intensity number selected for generating the X-rays, thereby setting the X-ray intensity of the structured anode.

Figure 2:
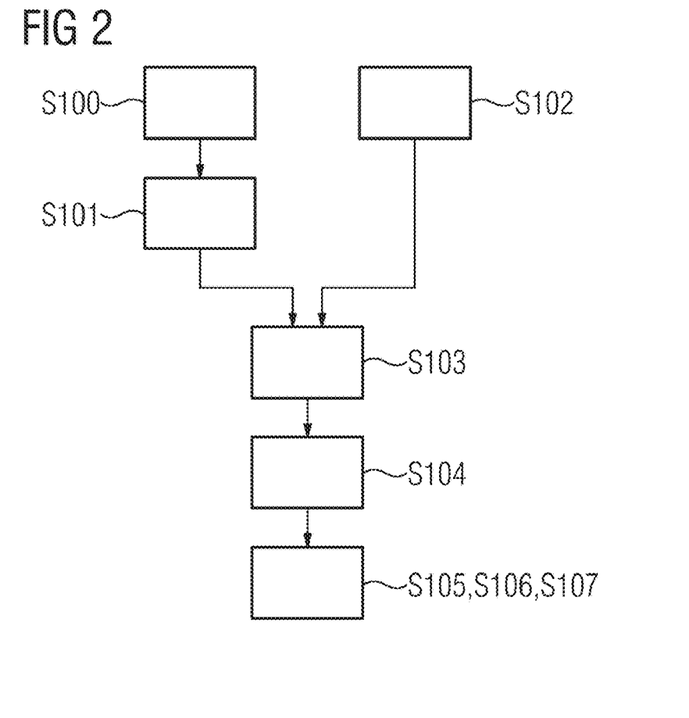
FIG. 2 shows a flowchart of the method for setting an X-ray intensity using a structured anode in a second example embodiment.

FIG. 2 shows in particular the first example embodiment according to FIG. 1 supplemented by the additional method steps S105 to S107 to produce the second example embodiment.

Method step S105 denotes that a second X-ray intensity setpoint is determined in the controller according to the patient undergoing the imaging scan, wherein a second setpoint X-ray intensity number is selected in the controller according to the second X-ray intensity setpoint and wherein the electron beam of the X-ray tube is re-aligned to the first anode microstructure or to the second anode microstructure according to the second setpoint X-ray intensity number selected.

Method step S106 denotes that the re-aligning of the electron beam according to the second setpoint X-ray intensity number selected takes place within an electron beam aligning time of less than 1 s after the aligning of the electron beam according to the first setpoint X-ray intensity number selected. In a particularly advantageous example embodiment, the electron beam aligning time is less than 1 ms.

Method step S107 denotes that the electron beam aligning time is matched to an X-ray detector read time of the imaging scan.

Figure 3:
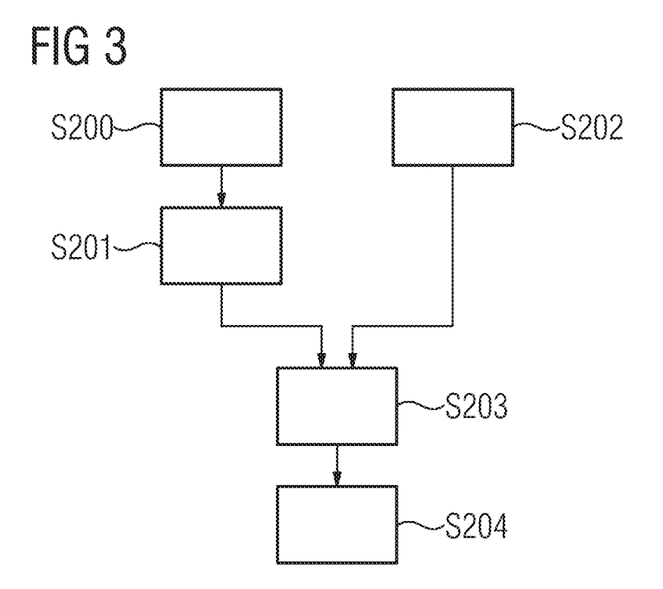
FIG. 3 shows a flowchart of a method for setting an X-ray intensity using a field emitter cathode in a third example embodiment.

FIG. 3 shows a flowchart of a method for setting an X-ray intensity using a field emitter cathode in a third example embodiment.

Method step S200 denotes providing a field emitter cathode.

Method step S201 denotes providing, in a controller, an X-ray intensity characteristic as a function of an emitter voltage dropped across the field emitter cathode.

Method step S202 denotes determining, in the controller, an X-ray intensity setpoint according to the patient undergoing an imaging scan.

Method step S203 denotes selecting the emitter voltage from the X-ray intensity characteristic according to the X-ray intensity setpoint.

Method step S204 denotes applying the emitter voltage selected to the field emitter cathode, thereby setting the X-ray intensity.

Figure 4:
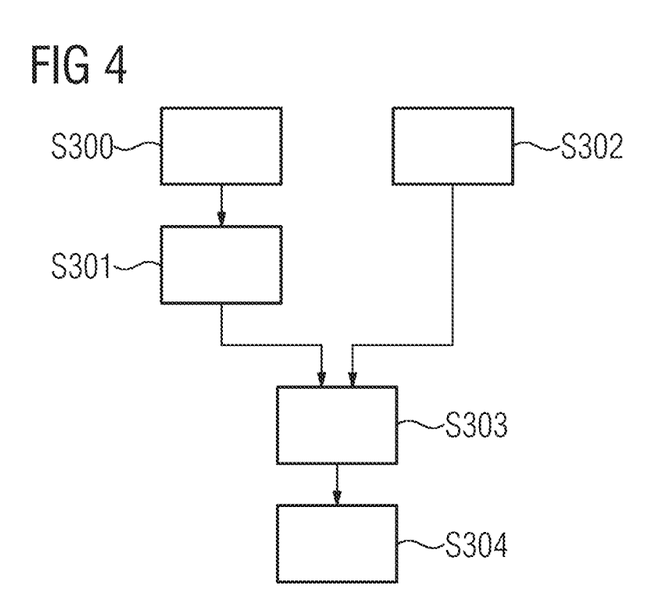
FIG. 4 shows a flowchart of a method for setting an X-ray intensity using a finger-shaped cathode head in a fourth [example embodiment]

FIG. 4 shows a flowchart of a method for setting an X-ray intensity using a finger-shaped cathode head in a fourth example embodiment.

Method step S300 denotes providing a meander-shaped emitter having a finger-shaped cathode head.

Method step S301 denotes providing, in a controller, an X-ray intensity characteristic as a function of a reverse voltage dropped across the finger-shaped cathode head.

Method step S302 denotes determining, in the controller, an X-ray intensity setpoint according to a patient undergoing an imaging scan.

Method step S303 denotes selecting the reverse voltage from the X-ray intensity characteristic according to the X-ray intensity setpoint.

Method step S304 denotes applying the reverse voltage selected to the finger-shaped cathode head, thereby setting the X-ray intensity.

Figure 5:
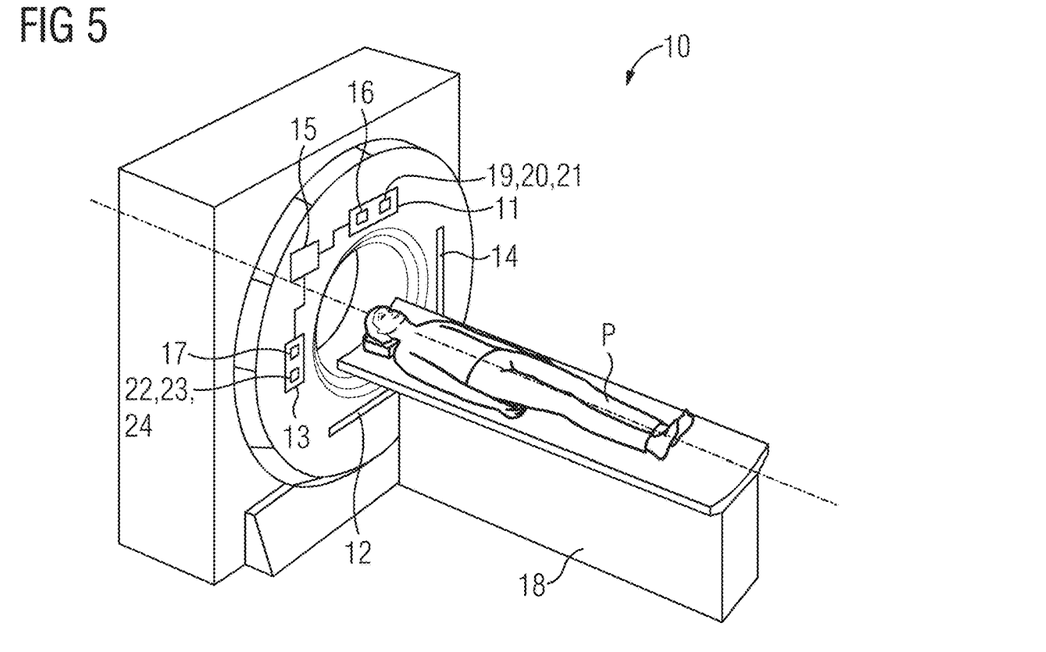
FIG. 5 shows an X-ray device.

FIG. 5 shows a perspective view of the X-ray device 10. In this example embodiment, the X-ray device 10 is designed as a dual X-ray tube CT scanner. The X-ray device 10 has an X-ray tube 11 and an X-ray detector 12. The X-ray device 10 also has another X-ray tube 13 and another X-ray detector 14. The X-ray device 10 has a controller 15 which is connected to a deflector 16 of the X-ray tube 11 and to a deflector 17 of the other X-ray tube 13. The deflector 16 and/or the deflector 17 can in each case be designed as an electromagnetic deflector or according to a Wehnelt cylinder.

A patient P is positioned on a patient table 18 during an imaging scan.

The X-ray tube 11 comprises a structured anode 19 having a first anode microstructure 20 and a second anode microstructure 21. The other X-ray tube 13 comprises another structured anode 22 having a third anode microstructure 23 and a fourth anode microstructure 24.

The X-ray tube 11 and the X-ray tube 13 are operated alternately. In particular, in addition to the method steps according to the example embodiment shown in FIG. 1, the other structured anode 22 having the third anode microstructure 23 and the fourth anode microstructure 24 is provided as part of the X-ray tube 13, wherein a third X-ray intensity number according to the third anode microstructure 23 and a fourth X-ray intensity number according to the fourth anode microstructure 24 is provided in the controller 15, wherein another setpoint of an X-ray intensity of the other structured anode 22 is determined in the controller 15 in a complementary manner to the first setpoint, wherein the third X-ray intensity number or the fourth X-ray intensity number is selected in the controller as another setpoint X-ray intensity number according to the other X-ray intensity setpoint, and wherein another electron beam of the other X-ray tube 13 is aligned to the third anode microstructure 23 or to the fourth anode microstructure 24 according to the other setpoint X-ray intensity number selected for generating the X-rays, thereby setting the X-ray intensity of the other structured anode 22.

Figure 6:
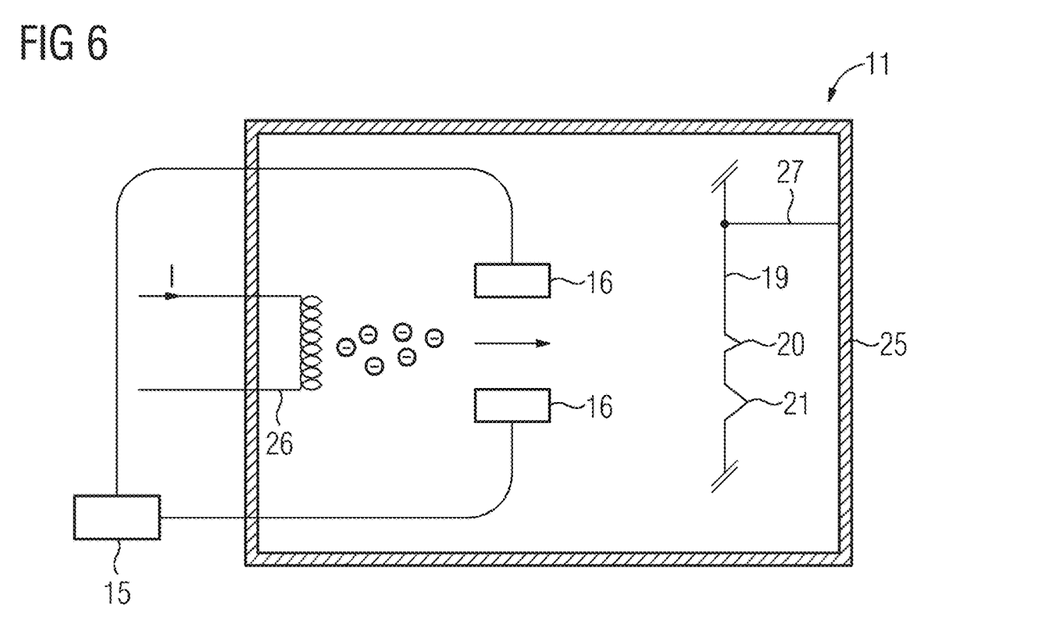
FIG. 6 shows the X-ray tube.

FIG. 6 shows a cross-sectional view of the X-ray tube 11 in another example embodiment.

The X-ray tube 11 has a housing 25. The housing 25 typically has an X-ray exit window through which the X-rays generated by way of the electron beam incident on the structured anode 19 can preferably emerge. The X-rays and the X-ray exit window are not shown in FIG. 6. Inside the housing 25 is a vacuum. Disposed inside the housing 25 is a cathode 26 having an emitter for emitting the electron beam using a heating current I. The deflector 16 is disposed and an acceleration voltage is applied between the cathode 26 and the structured anode 19. The deflector 16 can be the electromagnetic deflector or the Wehnelt cylinder. In this example embodiment, the first anode microstructure 20 differs from the second anode microstructure 21 in groove width and groove depth. Alternatively or in addition, the first anode microstructure 20 can differ from the second anode microstructure 21 in one of the following parameters:

center point distance, dotting of a groove.

In this example embodiment, the controller 15 is disposed outside the housing 25. The arrow indicates the electron beam direction. The structured anode 19 has an axis of rotation 27 and is e.g. of rotationally symmetrical design.

Although the invention has been illustrated and described in detail by the preferred example embodiments, the invention is not limited by the examples disclosed and other variations will be apparent to persons skilled in the art without departing from the scope of protection sought for the invention.

Although the invention has been illustrated and described in greater detail with reference to the referred example embodiments, the invention is not restricted thereby. Other variations and combinations can be derived herefrom by the person skilled in the art without departing from the essential concept of the invention.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for setting an X-ray intensity using a structured anode, comprising:

providing an X-ray tube including a structured anode, the structured anode including a first anode microstructure and a second anode microstructure;

providing, in a controller, a first X-ray intensity number according to the first anode microstructure and a second X-ray intensity number according to the second anode microstructure;

determining a first X-ray intensity setpoint in the controller according to a patient undergoing an imaging scan;

selecting, in the controller, the first X-ray intensity number or the second X-ray intensity number as a first setpoint X-ray intensity number, according to the first X-ray intensity setpoint determined; and aligning an electron beam of the X-ray tube to the first anode microstructure or to the second anode microstructure according to the first setpoint X-ray intensity number selected for generating the X-rays, thereby setting the X-ray intensity.

2. The method of claim 1, wherein a second X-ray intensity setpoint is determined in the controller according to the patient undergoing the imaging scan, wherein a second setpoint X-ray intensity number is selected according to the second X-ray intensity setpoint in the controller, and wherein the electron beam of the X-ray tube is re-aligned to the first anode microstructure or to the second anode microstructure according to the second setpoint X-ray intensity number selected.

3. The method of claim 2, wherein the electron beam is re-aligned according to the second setpoint X-ray intensity number selected within an electron beam aligning time of less than 1 s after the aligning of the electron beam according to the first setpoint X-ray intensity number selected.

4. The method of claim 3, wherein the electron beam aligning time is less than 1 ms.

5. The method of claim 4, wherein the electron beam aligning time is matched to an X-ray detector read time of the imaging scan.

6. The method of claim 3, wherein the electron beam aligning time is matched to an X-ray detector read time of the imaging scan.

7. The method of claim 2, wherein the first anode microstructure differs from the second anode microstructure in at least one of:
   groove depth,
   groove width,
   center point distance, and
   dotting of a groove.

8. The method of claim 2, wherein the electron beam is aligned via an electromagnetic deflector or via a Wehnelt cylinder.

9. The method of claim 2, wherein another structured anode, including a third anode microstructure and a fourth anode microstructure, is provided as part of another X-ray tube, wherein a third X-ray intensity number according to the third anode microstructure and a fourth X-ray intensity number according to the fourth anode microstructure is provided in the controller, wherein another setpoint of an X-ray intensity of the other structured anode is determined in the controller in a complementary manner to the first setpoint, wherein the third X-ray intensity number or the fourth X-ray intensity number is selected as another setpoint X-ray intensity number according to the other X-ray intensity setpoint in the controller, and wherein another electron beam of the other X-ray tube is aligned to the third anode microstructure or to the fourth anode microstructure according to the another setpoint X-ray intensity number selected for generating the X-rays, thereby setting the X-ray intensity of the another structured anode.

10. The method of claim 1, wherein the first anode microstructure differs from the second anode microstructure in at least one of:
    groove depth,
    groove width,
    center point distance, and
    dotting of a groove.

11. The method of claim 1, wherein the electron beam is aligned via an electromagnetic deflector or via a Wehnelt cylinder.

12. The method of claim 1, wherein another structured anode, including a third anode microstructure and a fourth anode microstructure, is provided as part of another X-ray tube, wherein a third X-ray intensity number according to the third anode microstructure and a fourth X-ray intensity number according to the fourth anode microstructure is provided in the controller, wherein another setpoint of an X-ray intensity of the other structured anode is determined in the controller in a complementary manner to the first setpoint, wherein the third X-ray intensity number or the fourth X-ray intensity number is selected as another setpoint X-ray intensity number according to the other X-ray intensity setpoint in the controller, and wherein another electron beam of the other X-ray tube is aligned to the third anode microstructure or to the fourth anode microstructure according to the another setpoint X-ray intensity number selected for generating the X-rays, thereby setting the X-ray intensity of the another structured anode.

13. A dual X-ray tube CT scanner, comprising:
    an X-ray tube;
    an X-ray detector;
    a controller; and
    another X-ray tube designed according to the method for setting the X-ray intensity of claim 12.

14. An X-ray device, comprising:
    the X-ray tube;
    an X-ray detector; and
    a controller, wherein the X-ray device is designed according to the method for setting the X-ray intensity of claim 1.

15. A single X-ray tube CT scanner, comprising:
    the X-ray device of claim 14.

16. A non-transitory computer program product, storing a computer program directly loadable into a memory of a at least one processor, the computer program including program code segments for carrying out the method of claim 1 when the computer program is executed in the at least one processor.

* * * * *